(12) United States Patent
Whittaker et al.

(10) Patent No.: US 9,408,631 B2
(45) Date of Patent: Aug. 9, 2016

(54) FLEXIBLE CANNULA AND OBTURATOR

(71) Applicant: DePuy Mitek, LLC, Raynham, MA (US)

(72) Inventors: Gregory R. Whittaker, Stoneham, MA (US); Steven N. Bittenson, Bedford, MA (US); Gary McAlister, Franklin, MA (US)

(73) Assignee: DePuy Mitek, LLC, Raynham, MA (US)

( * ) Notice: Subject to any disclaimer, the term of this patent is extended or adjusted under 35 U.S.C. 154(b) by 245 days.

(21) Appl. No.: 14/039,337

(22) Filed: Sep. 27, 2013

(65) Prior Publication Data

US 2015/0094543 A1 Apr. 2, 2015

(51) Int. Cl.
*A61B 17/34* (2006.01)

(52) U.S. Cl.
CPC ......... *A61B 17/3431* (2013.01); *A61B 17/3421* (2013.01); *A61B 17/3423* (2013.01); *A61B 2017/349* (2013.01); *A61B 2017/3445* (2013.01); *A61B 2017/3458* (2013.01)

(58) Field of Classification Search
CPC .................. A61B 17/3421; A61B 2017/3429; A61B 17/3431
See application file for complete search history.

(56) References Cited

U.S. PATENT DOCUMENTS

| 4,418,693 | A | 12/1983 | LeVeen |
| 5,069,224 | A | 12/1991 | Zinnanti, Jr. |
| 5,242,409 | A | 9/1993 | Buelna |
| 5,330,501 | A | 7/1994 | Tovey |
| 5,391,156 | A * | 2/1995 | Hildwein ............... A61B 17/29 411/503 |
| 5,423,848 | A * | 6/1995 | Washizuka ............. A61B 17/34 604/164.11 |
| 5,496,289 | A * | 3/1996 | Wenstrom, Jr. .... A61B 17/0483 604/264 |
| 5,634,911 | A | 6/1997 | Hermann |
| 5,634,937 | A | 6/1997 | Mollenauer |
| 5,871,474 | A | 2/1999 | Hermann |
| 5,919,183 | A | 7/1999 | Field |
| 6,468,292 | B1 | 10/2002 | Mollenauer |
| 7,174,889 | B2 | 2/2007 | Boedeker |
| 7,449,011 | B2 * | 11/2008 | Wenchell ........... A61B 17/3421 604/104 |
| 7,803,135 | B2 | 9/2010 | Franer |
| 2005/0043682 | A1 | 2/2005 | Kucklick |
| 2005/0268917 | A1 | 12/2005 | Boedeker |
| 2009/0204081 | A1 * | 8/2009 | Whittaker .......... A61B 17/3421 604/264 |
| 2010/0234669 | A1 * | 9/2010 | Armstrong ........... A61N 5/1007 600/7 |
| 2012/0095515 | A1 * | 4/2012 | Hamilton ............. A61B 17/864 600/304 |
| 2012/0157783 | A1 * | 6/2012 | Okoniewski ....... A61B 17/3423 600/208 |
| 2012/0323081 | A1 | 12/2012 | Son |

FOREIGN PATENT DOCUMENTS

| EP | 2090258 A1 | 8/2009 |
| EP | 2353527 A2 | 8/2011 |

* cited by examiner

*Primary Examiner* — Eduardo C Robert
*Assistant Examiner* — Julianna N Harvey

(57) ABSTRACT

A cannula system provides a cannula formed of a soft conformable material such as silicone and having an exterior thread. The cannula lacks rigidity, especially axially, and an obturator therefor is provided with an external thread to interact with the cannula an maintain its shape as it is inserted into a patient's body.

3 Claims, 2 Drawing Sheets

FLEXIBLE CANNULA AND OBTURATOR

BACKGROUND

The present invention relates to medical cannulas and more particularly to soft cannulas and obturators therefor.

Arthroscopy cannulas and mating obturators have traditionally been manufactured from rigid materials such as metals or rigid polymers. The cannula has a smooth inside diameter and the obturator has a smooth outside diameter. To insert the cannula into a patient, the obturator is placed into the cannula. The cannula/obturator is them "pushed" into the patient thru a small stab incision or portal.

Several potential issues exist with traditional rigid cannulas and obturators. Because they are rigid, they can be somewhat traumatic to the patients tissues. Additionally, as the patients joint swells with fluids during arthroscopy the cannulas tend to become loose in the portal and sometimes back out. Recently, several silicone (or other soft material) cannulas have been commercialized which attempt to address the existing limitations of rigid cannulas. However, the soft material has introduced new limitations.

The force required to insert cannula/obturator typically increases when the transition between the cannula and obturator reaches the patients skin. As the rigid cannula is introduced with increasing force to overcome such resistance it retains its shape due to its rigidity. However, soft and flexible cannulas cannot be inserted into a joint by the traditional means of inserting a obturator inside them and pushing them into the joint. When this is attempted, the soft, flexible cannula "accordions" on the obturator when its distal end hits the external skin. This problem is particularly evident when attempting to insert silicone cannulas which have a distal flange to prevent the cannula from backing out.

The typical method for inserting a silicone cannula with a distal flange is to grasp the distal end of the cannula with forceps, compress the distal flange and "jam" the cannula into the joint via the distal end. Thus, the cannula is pulled in from the distal end, not pushed in from the proximal end. This is an awkward insertion method that causes increased trauma to the portal site and often results in an enlarged portal.

SUMMARY OF THE INVENTION

A cannula system according to the present invention comprises cannula having an elongated tubular body with a cannulation extending axially therethrough. The body is formed of a flexible material. An obturator is sized to fit within the cannulation and has external threads which engage the cannula when the obturator is disposed within the cannulation.

Preferably, the cannula body has external threads. It can further be provided with pre-formed internal threads adapted to mate with the external threads of the obturator. In one aspect of the invention, the obturator is disposed within the cannula and the obturator external threads and the cannula external threads are in register with each other. Alternatively, the obturator external threads and the cannula external threads could have matching thread pitches that are out of register with each other such that the obturator external threads are disposed into the material of the cannula between the cannula external threads. The cannula can have a smooth interior surface in a relaxed configuration wherein the material of the cannula is sufficiently flexible such that temporary threads are formed within the cannulation by the obturator external threads when the obturator is disposed with the cannulation.

A method according to the present invention provides for insertion of a flexible cannula into a patient. The method comprises the steps of: a) threading an obturator having external threads thereon into a cannulation of a cannula that is formed of a flexible material; b) inserting the cannula, with the obturator disposed therein, through an incision in a patient's skin; c) maintaining an axial length of the cannula during step b) via an engagement between the cannula and the external threads on the obturator; and d) removing the obturator from the cannula and leaving the cannula disposed within the patient.

Preferably, the method further comprises engaging the patient with separate external threads on the cannula.

In one aspect of the invention, the cannula has internal threads within its cannulation and the engagement between the cannula and the external threads on the obturator comprises the external threads on the obturator mating with the internal threads within the cannulation. Alternatively, the cannula has no internal threads within its cannulation and the engagement between the cannula and the external threads on the obturator comprises material of the cannula deforming to engage with the external threads on the obturator.

DETAILED DESCRIPTION

Figure 2:
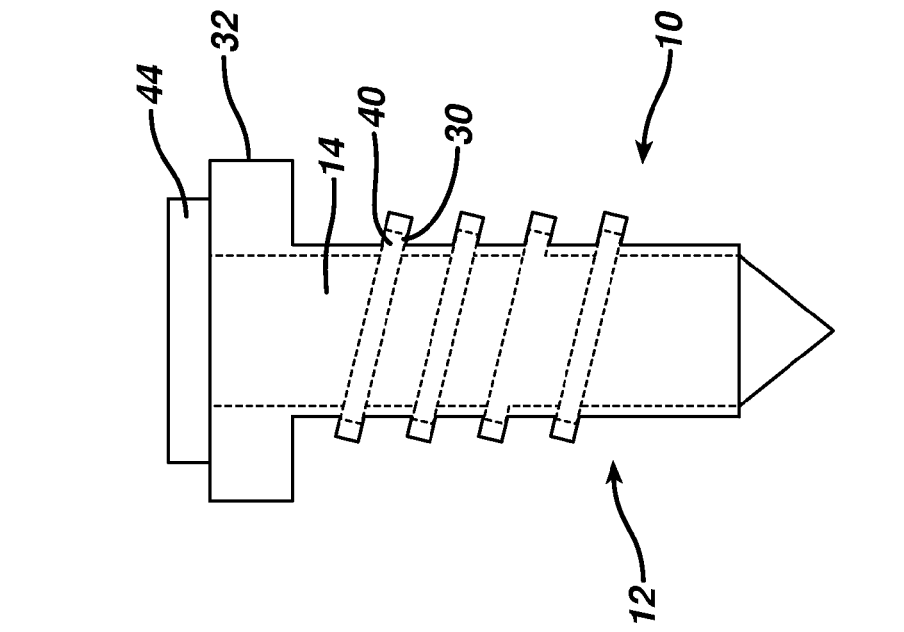
FIG. 2 is a side elevation view in cross-section of the cannula system of FIG. 1 showing the cannula and obturator thereof assembled together.
Figure 1:
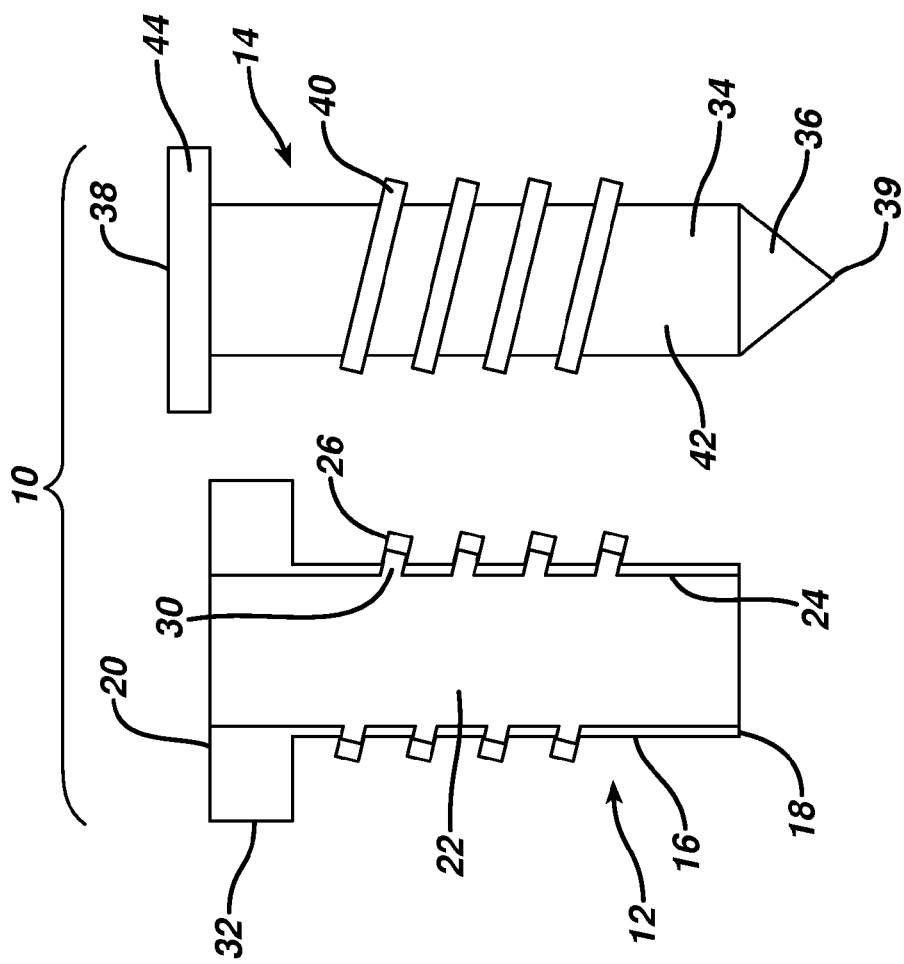
FIG. 1 is an exploded side elevation view of a cannula system according to the present invention.

FIGS. 1 and 2 illustrate a cannula system 10 comprising a cannula 12 and an obturator 14. The cannula 12 comprises an elongated tubular body 16 having a distal end 18 and proximal end 20. A cannulation 22 passes axially through the length of the body 16 creating an interior surface 24. External threads 26 encircle the body 16 from an exterior surface 28 thereof. The threads 26 assists in holding the cannula 12 in place after it is placed through a patient's skin (not shown in FIGS. 1 and 2). Internal threads 30 are formed into the interior surface 24 of the cannulation 22. A radially extending flange 32 is provided at the proximal end 20. Optionally, a distal flange (not shown) similar to the proximal flange 32 could also be provided on the cannula 12.

The obturator 14 comprises a cylindrical body 34 sized to fit within the cannulation 22 of the cannula 12. The body 34 has a distal end 36 and proximal end 38. The distal end 36 tapers to a blunt tip 39 to assist in insertion of the cannula system 10. The concepts of the present invention would apply as well if a trocar with a sharp tip were substituted for the obturator 14 and thus when employed in connection with the invention as described herein the term "obturator" is generally understood to encompass broadly any rigid cannula insertion aid, be its tip blunt or sharp. External threads 40 encircle an exterior 42 of the body and mate with the internal threads 30 of the cannula 12. A radial flange 44 at the body proximal end 38 abuts the flange 32 on the cannula 12 when the obturator 14 is fully inserted therein.

The cannula 12 is formed of a soft and flexible material, such as a medical grade silicone, to protect the patient's tissue and to enhance maneuverability of the surgical procedure being performed therethrough. The obturator 14 is formed of a rigid material such as a medical grade polymer or metals. Pushing such a soft material through an incision in a patient's skin and into a joint space would be difficult with a normal smooth obturator as the material lacks axial rigidity and would tend to bunch up and compress accordion style. With the threaded obturator 14 affixed within the cannula 12 the two are coupled together so that the length of the cannula 12 is maintained during insertion allowing it to be inserted as would a normal rigid cannula without deforming unacceptably.

In use, a small incision of about 2 to 3 mm is made through the skin and the cannula system with the obturator 14 received within the cannula 12 is pushed through the incision and past interior tissue to a working location inside a patient's body such as into a joint space. The interaction of the obturator threads 40 and the soft cannula 12 maintains the shape of the cannula 12 as it is inserted. After the cannula 12 is properly positioned the obturator 14 is removed leaving the cannula 12 in place for receipt of an arthroscope or surgical instruments as desired.

Figure 3:
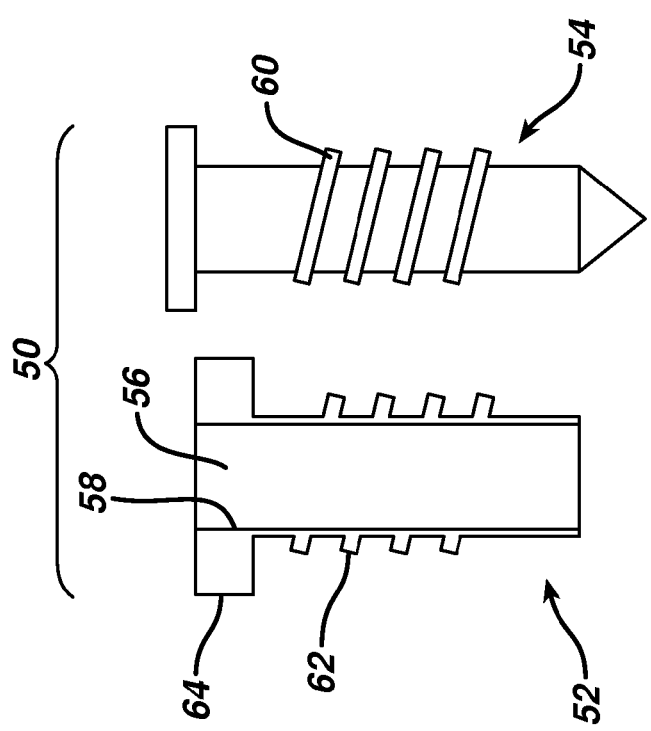
FIG. 3. Is an exploded side elevation view of an alternative embodiment of a cannula system according to the present invention.

FIG. 3 illustrates an alternative embodiment of a cannula system 50 according to the present invention which comprises a cannula 52 and obturator 54. The main difference with the cannula system 10 is that the cannula 52 has a cannulation 56 with a smooth interior surface 58 without internal threads. The obturator 54 has external threads 60 which can still mate well with the cannula 52 due to the soft material from which it is formed that allows it to conform to the threads 60. The cannula 52 retains exterior threads 62 and proximal flange 64.

Figure 4B:
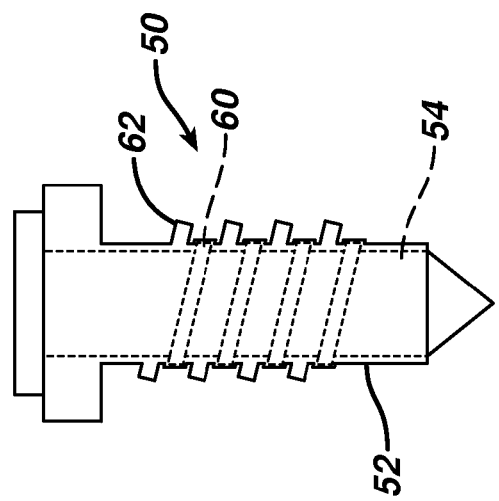
FIG. 4B is a side elevation view in cross-section of the cannula system of FIG. 3 showing the cannula and obturator thereof assembled together with their respective threads offset.
Figure 4A:
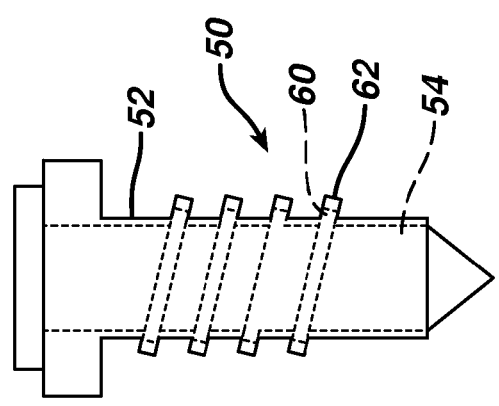
FIG. 4A is a side elevation view in cross-section of the cannula system of FIG. 3 showing the cannula and obturator thereof assembled together with their respective threads aligned.

The threads 60 of the obturator 54 can have similar thread pitch as the threads 62 of the cannula 52 and be threaded with the threads 60 and 62 in alignment or register with each other as shown in FIG. 4A or longitudinally offset as shown in FIG. 4B such that the obturator threads 60 are disposed into the material of the cannula 52 between the cannula threads 62. In the latter case the soft material between the threads 62 of the cannula 52 would form temporary internal threads with the obturator 54 in place. In either event, once the obturator 54 is removed the cannulation would revert to its smooth configuration easing insertion of instruments therethrough. The threads 60 and 62 could also be of different dimensions, such as varying thread pitch such that they do not interact with each other as the obturator 54 is threaded into the cannula 52.

While the invention has been particularly described in connection with specific embodiments thereof, it is to be understood that this is by way of illustration and not of limitation, and that the scope of the appended claims should be construed as broadly as the prior art will permit. For instance, the obturator 14 is shown with threads 40 along most of the length of its interaction with the cannula 12. However, it would work well if the threads 40 were provided only near its distal end 36 as it would still maintain the cannula's 12 length during insertion

What is claimed is:

1. A method of inserting a flexible cannula into a patient comprising the steps of:
    a) threading an obturator having external threads thereon into a cannulation of a cannula that is formed of a flexible material, the obturator external threads forming secondary threads on the cannula;
    b) inserting the cannula, with the obturator disposed therein, through an incision in a. patient's skin, the secondary threads engaging the patient;
    c) maintaining an axial length of the cannula during step b) via an engagement between the cannula and the external threads on the obturator; and
    d) removing the obturator from the cannula and leaving the cannula disposed within the patient.

2. A method according to claim 1 wherein the cannula has internal threads within its cannulation and the engagement between the cannula and the external threads on the obturator comprises the external threads on the obturator mating with the internal threads within the cannulation.

3. A method according to claim 1 wherein the cannula has no internal threads within its cannulation and the engagement between the cannula and the external threads on the obturator comptises material of the cannula deforming to engage with the external threads on the obturator.

* * * * *